United States Patent
De Peretti et al.

(10) Patent No.: US 8,507,520 B2
(45) Date of Patent: Aug. 13, 2013

(54) POLYSUBSTITUTED 2-ARYL-6-PHENYLIMIDAZO[1,2-A]PYRIDINE DERIVATIVES, AND PREPARATION AND THERAPEUTIC USE THEREOF

(75) Inventors: Danielle De Peretti, Paris (FR); Yannick Evanno, Paris (FR); Patrick Lardenois, Paris (FR); Nathalie Rakotoarisoa, Paris (FR); Antonio Almario Garcia, Paris (FR); André Malanda, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/881,827

(22) Filed: Sep. 14, 2010

(65) Prior Publication Data

US 2011/0065745 A1   Mar. 17, 2011

Related U.S. Application Data

(63) Continuation of application No. PCT/FR2009/000302, filed on Mar. 20, 2009.

(30) Foreign Application Priority Data

Mar. 21, 2008   (FR) .................... 08 01581

(51) Int. Cl.
- *C07D 491/02* (2006.01)
- *C07D 498/02* (2006.01)
- *A01N 43/42* (2006.01)
- *A61K 31/44* (2006.01)

(52) U.S. Cl.
USPC ............. 514/300; 546/14; 546/121; 546/311

(58) Field of Classification Search
USPC ............................ 514/300; 546/14, 121, 311
See application file for complete search history.

(56) References Cited

U.S. PATENT DOCUMENTS

| | | | |
|---|---|---|---|
| 7,902,219 B2 | 3/2011 | Peyronel et al. | |
| 7,915,284 B2 * | 3/2011 | Almario Garcia et al. | ... 514/300 |
| 2009/0253735 A1 | 10/2009 | Almario-Garcia et al. | |
| 2010/0168155 A1 | 7/2010 | El-Ahmad et al. | |
| 2011/0065699 A1 * | 3/2011 | De Peretti et al. ......... | 514/233.2 |
| 2011/0065700 A1 | 3/2011 | De Peretti et al. | |
| 2011/0065727 A1 | 3/2011 | De Peretti et al. | |

FOREIGN PATENT DOCUMENTS

| | | |
|---|---|---|
| FR | 2 903 105 | 1/2008 |
| FR | 2 903 107 | 1/2008 |
| WO | WO 2004/076412 A2 | 9/2004 |
| WO | 2008034974 * | 3/2008 |
| WO | WO 2008/034974 A1 | 3/2008 |

OTHER PUBLICATIONS

Gudmundsson et al, An Improved Synthesis of 2-Chlorinated Imidazo[1,2-a]pyridines and the Application of this Procedure for the Synthesis of Several New Polychlorinated Imidazo[1,2-a]pyridines, Syn. Comm., 1997 (27) 10, pp. 1763-1775.
Barber et al, Catalysts for Suzuki-Miyaura Coupling Processes: Scope and Studies of the Effect of Ligand Structure, JACS, 2005(127) pp. 4685-4696.
Cai et al, Synthesis and Structure-Affinity Relationships of New 4-(6-Iodo-H-imidazo[1,2-a]pyridin-2-yl)-N-dimethylbenzeneamine Derivatives as Ligands for Human b-Amyloid plaques, J. Med. Chem., 2007 (50) pp. 4746-4758.
Dimauro et al, Microwave-Assisted Preparation of Fused Bicyclic Heteroaryl Boronates: Application in One-Pot Suzuki Couplings; JOC, 2006(71) pp. 3959-5962.
Enguehard et al, (Hetero)Arylation of 6-Halagenoimidazo [1,2-a]Pyridines Differently Substituted at C(2): Influence of the 2-Substituent on the Suzuki Cross-Coupling Reaction, Helvetica Chimica Acta, 2001(84) pp. 3610-3615.
Fisher et al, Imidaza[1,2-a]pynidine Anthelmintic and Antifungal Agents, J.Med.Chem., 1972 (15) 9, pp. 982-985.
International Search Report for WO2009/144394 dated Dec. 3, 2009.
U.S. Appl. No. 12/881,805—Notice of Allowance dated Dec. 30, 2011.
U.S. Appl. No. 12/881,805—Non-Final Office Action dated Sep. 7, 2011.

* cited by examiner

*Primary Examiner* — Niloofar Rahmani
(74) *Attorney, Agent, or Firm* — Kelly L. Bender

(57) ABSTRACT

Compounds of formula (I):

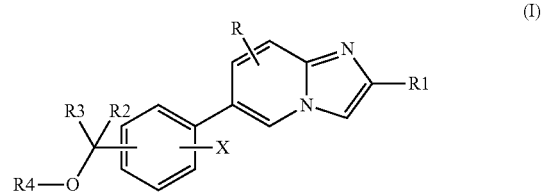

wherein R, $R_1$, $R_2$, $R_3$, $R_4$, and X are as defined in the disclosure, or an acid addition salt thereof, and the therapeutic use and process of synthesis thereof.

12 Claims, No Drawings

POLYSUBSTITUTED 2-ARYL-6-PHENYLIMIDAZO[1,2-A]PYRIDINE DERIVATIVES, AND PREPARATION AND THERAPEUTIC USE THEREOF

This application is a continuation of International application No. PCT/FR2009/000302, filed Mar. 20, 2009, which is incorporated herein by reference in its entirety; which claims the benefit of priority of French Patent Application No. 0801581, filed Mar. 21, 2008.

The present invention relates to polysubstituted 2-aryl-6-phenylimidazo[1,2-α]pyridine derivatives, to the preparation thereof and to the therapeutic use thereof in the treatment or prevention of diseases involving Nurr-1 nuclear receptors, also known as NR4A2, NOT, TINUR, RNR-1 and HZF3.

The subject of the present invention is the compounds of formula (I):

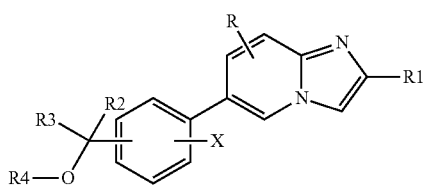

in which:
  $R_1$ represents a phenyl group or a naphthyl group, it being possible for these two groups to be optionally substituted with one or more atoms or groups chosen, independently of one another, from the following atoms or groups: halogen, $(C_1-C_{10})$alkyl, halo$(C_1-C_{10})$alkyl, $(C_1-C_{10})$alkoxy, halo$(C_1-C_{10})$alkoxy, $(C_1-C_{10})$thioalkyl, —S(O)$(C_1-C_{10})$alkyl, —S(O)$_2$($C_1-C_{10}$-alkyl), hydroxyl, cyano, nitro, hydroxy$(C_1-C_{10})$alkylene, NRaRb$(C_1-C_{10})$alkylene, $(C_1-C_{10})$alkoxy$(C_1-C_{10})$alkylenoxy, NRaRb, CONRaRb, SO$_2$NRaRb, NRcCORd, OC(O)NRaRb, OCO$(C_1-C_{10})$alkyl, NRcC(O)ORe, NRcSO$_2$Re, aryl$(C_1-C_{10})$alkylene, monocyclic heteroaryl or aryl, the monocyclic heteroaryl or aryl being optionally substituted with one or more substituents chosen from a halogen, and a $(C_1-C_{10})$ alkyl, halo$(C_1-C_{10})$alkyl, $(C_1-C_{10})$alkoxy, halo$(C_1-C_{10})$alkoxy, NRaRb, hydroxyl, oxo, nitro, cyano or OCO$(C_1-C_{10})$alkyl group;
  X represents from 1 to 4 substituents, which are identical to or different from one another, chosen from hydrogen, halogen, $(C_1-C_{10})$alkyl, $(C_1-C_{10})$alkoxy, NRaRb, cyano and nitro, it being possible for the $(C_1-C_{10})$alkyl to be optionally substituted with one or more groups chosen from a halogen, $(C_1-C_{10})$alkoxy, halo$(C_1-C_{10})$alkoxy, NRaRb or hydroxyl;
  R represents, at position 3, 5, 7 or 8 of the imidazo[1,2-α]pyridine, from 1 to 4 substituents, which are identical to or different from one another, chosen from a halogen, $(C_1-C_{10})$alkyl, halo$(C_1-C_{10})$alkyl and $(C_1-C_{10})$alkoxy;
  $R_2$ and $R_3$ represent, independently of one another,
    a hydrogen atom;
    a $(C_1-C_{10})$alkyl group, optionally substituted with an Rf group;
    an aryl group, optionally substituted with one or more substituents chosen from a halogen, and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro or cyano group;
  $R_2$ and X can form, together with the carbon atoms which bear them, a carbon-based ring containing from 5 to 7 carbon atoms;
  $R_4$ represents:
    a hydrogen atom;
    a $(C_1-C_{10})$alkyl group, optionally substituted with an Rf group;
    an aryl group, optionally substituted with one or more substituents chosen from a halogen, and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro, cyano, $(C_1-C_{10})$alkyl(CO)—, CONRaRb, NRcCORd, OC(O)NRaRb, OCO$(C_1-C_{10})$alkyl, NRcC(O)ORe or aryl group, the aryl being optionally substituted with one or more substituents chosen from a halogen, and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro or cyano group;
  Ra and Rb represent, independently of one another, a hydrogen atom or a $(C_1-C_{10})$alkyl, aryl$(C_1-C_{10})$alkylene or aryl group;
  or Ra and Rb form, together with the nitrogen atom which bears them, an azetidine, pyrrolidine, piperidine, azepine, morpholine, thiomorpholine, piperazine or homopiperazine group, this group being optionally substituted with a $(C_1-C_{10})$alkyl, aryl or aryl$(C_1-C_{10})$alkylene group;
  Rc and Rd represent, independently of one another, a hydrogen atom or a $(C_1-C_{10})$alkyl, aryl$(C_1-C_{10})$alkylene or aryl group,
  or Rc and Rd together form a $(C_2-C_5)$alkylene group;
  Re represents a $(C_1-C_{10})$alkyl, aryl$(C_1-C_{10})$alkylene or aryl group,
  or Rc and Re together form a $(C_2-C_5)$alkylene group;
  Rf represents a halogen atom, or a $(C_1-C_{10})$alkoxy, halo$(C_1-C_{10})$alkoxy, hydroxyl, cyano, NRaRb, C(O)NRaRb, NRcCORd, OC(O)NRaRb, OCO$(C_1-C_{10})$alkyl, NRcCOORe, SO$_2$NRaRb, NRcSO$_2$Re, aryl$(C_1-C_{10})$alkylene or aryl group, the aryl being optionally substituted with one or more substituents chosen from a halogen, and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro, cyano or OCO$(C_1-C_{10})$alkyl group;

in the form of a base or of an addition salt with an acid.

The compounds of formula (I) can comprise one or more asymmetrical carbon atoms. They can therefore exist in the form of enantiomers or of diastereoisomers. These enantiomers and diastereoisomers, and also mixtures thereof, including racemic mixtures, are part of the invention.

The compounds of formula (I) can exist in the form of bases or of addition salts with acids. Such addition salts are part of the invention.

These salts can be prepared with pharmaceutically acceptable acids, but the salts of other acids that are useful, for example, for purifying or isolating the compounds of formula (I) are also part of the invention.

The compounds of formula (I) can also exist in the form of hydrates or of solvates, i.e. in the form of associations or of combinations with one or more water molecules or with a solvent. Such hydrates and solvates are also part of the invention.

In the context of the present invention:
  the term "a $(C_x-C_t)$ group" is intended to mean: a group containing between x and t carbon atoms;
  the term "a halogen atom" is intended to mean: a fluorine, a chlorine, a bromine or an iodine;
  the term "an alkyl group" is intended to mean: a linear, branched or cyclic, saturated aliphatic group optionally substituted with a linear, branched or cyclic, saturated alkyl group. By way of examples, mention may be made of methyl, ethyl, propyl, isopropyl, butyl, isobutyl, tert-butyl, cyclopropyl, cyclobutyl, cyclopentyl, cyclohexyl, methylcyclopropyl, cyclopropylmethyl, etc, groups;

the term "an alkylene group" is intended to mean: a divalent alkyl group;

the term "an alkoxy group" is intended to mean: an —O-alkyl radical wherein the alkyl radical is as defined above;

the term "a haloalkyl group" is intended to mean: an alkyl group substituted with one or more halogen atoms, which are identical or different. By way of examples, mention may be made of $CF_3$, $CH_2CF_3$, $CHF_2$ or $CCl_3$ groups;

the term "a haloalkoxy group is intended to mean: an —O-alkyl radial wherein the alkyl group is as defined above and substituted with one or more halogen atoms, which are identical or different. By way of examples, mention may be made of $OCF_3$, $OCHF_2$ or $OCCl_3$ groups;

the term "a thioalkyl group" is intended to mean: an S-alkyl radical wherein the alkyl group is as defined above;

the term "an aryl group" is intended to mean: a monocyclic or bicyclic aromatic group containing from 6 to 10 atoms. By way of examples of aryl groups, mention may be made of phenyl and naphthyl;

the term "a heteroaryl group" is intended to mean: a monocyclic or bicyclic aromatic group containing from 5 to 10 atoms, including from 1 to 4 heteroatoms chosen from N, O and S. By way of examples of monocyclic heteroaryl groups, mention may be made of: pyrrole, furan, thiophene, pyrazole, imidazole, triazole, tetrazole, oxazole, isoxazole, oxadiazole, thiazole, isothiazole, thiadiazole, pyridine, pyrimidine, pyrazine, pyridazine or triazine;

the sulphur and nitrogen atoms may be in the oxidized state (N-oxide, sulphoxide, sulphone).

Among the compounds of formula (I) which are subjects of the invention, a first group of compounds is constituted of the compounds for which:

$R_1$ represents a phenyl group or a naphthyl group, optionally substituted with one or more atoms or groups chosen, independently of one another, from halogen atoms or ($C_1$-$C_{10}$)alkyl, ($C_1$-$C_{10}$) alkoxy or halo($C_1$-$C_{10}$)alkoxy groups;

the other substituents being as defined above.

Among the compounds of formula (I) which are subjects of the invention, a second group of compounds is constituted of the compounds for which:

$R_1$ represents a phenyl group or a naphthyl group, the phenyl group being optionally substituted, at position 2, 3 or 4, with one or more atoms or groups chosen, independently of one another, from halogen atoms or ($C_1$-$C_{10}$)alkyl, ($C_1$-$C_{10}$)alkoxy or halo($C_1$-$C_{10}$)alkoxy groups;

the other substituents being as defined above.

Among the compounds of formula (I) which are subjects of the invention, a third group of compounds is constituted of the compounds for which:

$R_1$ represents a phenyl group or a naphthyl group, optionally substituted with one or more atoms or groups chosen, independently of one another, from halogen atoms or methoxy, methyl or difluoromethyloxy groups;

the other substituents being as defined above.

Among the compounds of formula (I) which are subjects of the invention, a fourth group of compounds is constituted of the compounds for which:

$R_1$ represents a phenyl group or a naphthyl group, the phenyl group being optionally substituted, at position 2, 3 or 4, with one or more atoms or groups chosen, independently of one another, from halogen atoms or methoxy, methyl or difluoromethyloxy groups; the other substituents being as defined above.

Among the compounds of formula (I) which are subjects of the invention, a fifth group of compounds is constituted of the compounds for which:

X represents 1 or 2 substituent(s) which are identical to or different from one another, chosen from hydrogen or halogen atoms;

the other substituents being as defined above.

Among the compounds of formula (I) which are subjects of the invention, a sixth group of compounds is constituted of the compounds for which:

X represents 1 or 2 substituent(s), which are identical to or different from one another, chosen from hydrogen or fluorine atoms;

the other substituents being as defined above.

Among the compounds of formula (I) which are subjects of the invention, a seventh group of compounds is constituted of the compounds for which:

R represents, at position 3, 7 or 8 of the imidazo[1,2-α] pyridine, 1 or 2 substituent(s), which are identical to or different from one another, chosen from halogen atoms or ($C_1$-$C_{10}$)alkyl groups;

the other substituents being as defined above.

Among the compounds of formula (I) which are subjects of the invention, an eighth group of compounds is constituted of the compounds for which:

R represents, at position 3, 7 or 8 of the imidazo[1,2-α] pyridine, a substituent chosen from halogen atoms or ($C_1$-$C_{10}$)alkyl groups;

the other substituents being as defined above.

Among the compounds of formula (I) which are subjects of the invention, a ninth group of compounds is constituted of the compounds for which:

R represents, at position 3, 7 or 8 of the imidazo[1,2-α] pyridine, a substituent chosen from halogen atoms or a methyl group;

the other substituents being as defined above.

Among the compounds of formula (I) which are subjects of the invention, a tenth group of compounds is constituted of the compounds for which:

$R_2$ and $R_3$ represent, independently of one another, a hydrogen atom or a ($C_1$-$C_{10}$)alkyl group;

the other substituents being as defined above.

Among the compounds of formula (I) which are subjects of the invention, an eleventh group of compounds is constituted of the compounds for which:

$R_2$ and $R_3$ represent, independently of one another, a hydrogen atom or a methyl group;

the other substituents being as defined above.

Among the compounds of formula (I) which are subjects of the invention, a twelfth group of compounds is constituted of the compounds for which:

$R_4$ represents a hydrogen atom or a ($C_1$-$C_{10}$)alkyl group;

the other substituents being as defined above.

Among the compounds of formula (I) which are subjects of the invention, a thirteenth group of compounds is constituted of the compounds for which:

$R_4$ represents a hydrogen atom or a methyl group;

the other substituents being as defined above.

Among the compounds of formula (I) which are subjects of the invention, a fourteenth group of compounds is constituted of the compounds for which:

the group

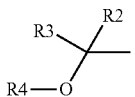

is at position 2, 3 or 4 on the phenyl nucleus which bears it; the other substituents of the compounds of formula (I) being as defined above.

Among the compounds of formula (I) which are subjects of the invention, a fifteenth group of compounds is constituted of the compounds for which:

$R_1$ represents a phenyl group or a naphthyl group, optionally substituted with one or more atoms or groups chosen, independently of one another, from halogen atoms or ($C_1$-$C_{10}$)alkyl, ($C_1$-$C_{10}$) alkoxy or halo ($C_1$-$C_{10}$)alkoxy groups;

X represents 1 or 2 substituent(s), which may be identical to or different from one another, chosen from hydrogen or halogen atoms;

R represents, at position 3, 7 or 8 of the imidazo[1,2-α]pyridine, a substituent chosen from halogen atoms or ($C_1$-$C_{10}$)alkyl groups;

$R_2$ and $R_3$ represent, independently of one another, a hydrogen atom or a ($C_1$-$C_{10}$)alkyl group;

$R_4$ represents a hydrogen atom or a ($C_1$-$C_{10}$)alkyl group; the group

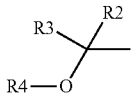

is at position 2, 3 or 4 on the phenyl nucleus which bears it; in the form of a base or an addition salt with an acid.

Among the compounds of formula (I) which are subjects of the invention, a sixteenth group of compounds is constituted of the compounds for which:

$R_1$ represents a phenyl group or a naphthyl group, the phenyl group being optionally substituted, at position 2, 3 or 4, with one or more atoms or groups chosen, independently of one another, from halogen atoms or methoxy, methyl or difluoromethyloxy groups;

X represents 1 or 2 substituent(s), which are identical to or different from one another, chosen from hydrogen or fluorine atoms;

R represents, at position 3, 7 or 8 of the imidazo[1,2-α] pyridine, a substituent chosen from halogens or a methyl group;

$R_2$ and $R_3$ represent, independently of one another, a hydrogen atom or a methyl group;

$R_4$ represents a hydrogen atom or a methyl group; the group

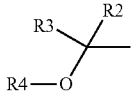

is at position 2, 3 or 4 on the phenyl nucleus which bears it; in the form of a base or of an addition salt with an acid.

Among the compounds of formula (I) which are subjects of the invention, a seventeenth group of compounds is constituted of the compounds for which:

$R_1$ represents a phenyl group or a naphthyl group, it being possible for these two groups to be optionally substituted with one or more atoms or groups chosen, independently of one another, from the following atoms or groups: halogen, ($C_1$-$C_{10}$)alkyl, ($C_1$-$C_{10}$)alkoxy and halo($C_1$-$C_{10}$)alkoxy;

X represents a hydrogen atom;

R is at position 3, 7 or 8 of the imidazo[1,2-α]pyridine and represents a ($C_1$-$C_{10}$)alkyl;

$R_2$ and $R_3$ represent, independently of one another, a hydrogen atom;

$R_4$ represents a hydrogen atom;

in the form of a base or of an addition salt with an acid.

Among the compounds of formula (I) which are subjects of the invention, mention may in particular be made of the following compounds:

{3-[2-(4-chlorophenyl)-8-methylimidazo[1,2-α]pyridin-6-yl]phenyl}methanol;

{3-[2-(4-chlorophenyl)-7-methylimidazo[1,2-α]pyridin-6-yl]phenyl}methanol;

[3-(3-methyl-2-phenylimidazo[1,2-α]pyridin-6-yl)phenyl]methanol;

{3-[2-(2,4-difluorophenyl)-3-methylimidazo[1,2-α]pyridin-6-yl]phenyl}methanol and the hydrochloride thereof;

{3-[2-(4-chloro-3-methylphenyl)-3-methylimidazo[1,2-α]pyridin-6-yl]phenyl}methanol and the hydrochloride thereof;

{3-[2-(4-chlorophenyl)-3-methylimidazo[1,2-α]pyridin-6-yl]phenyl}methanol and the hydrochloride thereof;

{3-[2-(4-methoxyphenyl)-3-methylimidazo[1,2-α]pyridin-6-yl]phenyl}methanol and the hydrochloride thereof;

{3-[2-[4-(difluoromethyloxy)phenyl]-3-methylimidazo[1,2-α]pyridin-6-yl]phenyl}methanol and the hydrochloride thereof;

[3-(8-methyl-2-naphthyl-2-ylimidazo[1,2-α]pyridin-6-yl)phenyl]methanol;

[4-(8-methyl-2-naphthyl-2-ylimidazo[1,2-α]pyridin-6-yl)phenyl]methanol;

2-[3-(3-methyl-2-phenylimidazo[1,2-α]pyridin-6-yl)phenyl]propan-2-ol;

2-{3-[2-(4-chlorophenyl)-3-methylimidazo[1,2-α]pyridin-6-yl]phenyl}propan-2-ol;

2-{3-[2-(3-chlorophenyl)-3-methylimidazo[1,2-α]pyridin-6-yl]phenyl}propan-2-ol;

2-{3-[2-(2,4-difluorophenyl)-3-methylimidazo[1,2-α]pyridin-6-yl]phenyl}propan-2-ol;

2-{3-[2-(4-methoxyphenyl)-3-methylimidazo[1,2-α]pyridin-6-yl]phenyl}propan-2-ol;

{2-fluoro-6-[2-(4-methoxyphenyl)-3-methylimidazo[1,2-α]pyridin-6-yl]phenyl}methanol;

[2,6-difluoro-3-(3-methyl-2-phenylimidazo[1,2-α]pyridin-6-yl)phenyl]methanol;

{3-[2-(4-chlorophenyl)-3-methylimidazo[1,2-α]pyridin-6-yl]-2,6-difluorophenyl}methanol;

{3-[2-(3-chlorophenyl)-3-methylimidazo[1,2-α]pyridin-6-yl]-2,6-difluorophenyl}methanol;

{2,6-difluoro-3-[2-(4-methoxyphenyl)-3-methylimidazo[1,2-α]pyridin-6-yl]-phenyl}methanol;

{3-[3-chloro-2-(4-chlorophenyl)imidazo[1,2-α]pyridin-6-yl]phenyl}methanol;

2-{3-[2-(4-chlorophenyl)-3-fluoroimidazo[1,2-α]pyridin-6-yl]phenyl}propan-2-ol;

2-{3-[3-chloro-2-(4-chlorophenyl)imidazo[1,2-α]pyridin-6-yl]phenyl}propan-2-ol;

[2-fluoro-6-(3-methyl-2-phenylimidazo[1,2-α]pyridin-6-yl)phenyl]methanol;

{2-[2-(4-chlorophenyl)-3-methylimidazo[1,2-α]pyridin-6-yl]-6-fluorophenyl}methanol;

{2-[2-(3-chlorophenyl)-3-methylimidazo[1,2-α]pyridin-6-yl]-6-fluorophenyl}methanol;
{2-[2-(2,4-difluorophenyl)-3-methylimidazo[1,2-α]pyridin-6-yl]-6-fluorophenyl}methanol;
3-chloro-6-(3-methoxymethylphenyl)-2-(4-chlorophenyl)imidazo[1,2-α]pyridine;
{3-[3-chloro-2-(4-chlorophenyl)imidazo[1,2-α]pyridin-6-yl]-2,6-difluorophenyl}methanol.

In accordance with the invention, the compounds of general formula (I) can be prepared according to the process described in scheme 1.

The compounds of the invention can be prepared according to scheme 1 by means of a cupping reaction, catalysed by metal such as palladium, between an imidazopyridine of general formula (IV), in which R and R1 are defined as above and Hal represents a halogen atom, and a derivative of general formula (VII), in which R2, R3, R4 and X are defined as above and Y represents a boron or tin derivative, so as to obtain the compounds of general formula (I), for example according to the method described by A. Gueiffier in *Helv. Chim. Acta* 2001, 84, 3610-3615.

The compounds of general formula (IV) can be obtained by condensation between an aminopyridine of general formula (II), in which R is defined as above and Hal represents a halogen atom, and a bromoketone of general formula (III), in which R1 is defined as above, for example according to the methods described by L. Cai in *J. Med. Chem.* 2007, 50, 4746, so as to obtain the compounds of general formula (IV), for which R is at position 5, 7 or 8 of the imidazopyridine nucleus. The compounds of general formula (IV), for which R is at position 3 of the imidazopyridine nucleus, can be obtained by condensation between an aminopyridine of general formula (V), in which Hal represents a halogen atom, and a bromoketone of general formula (VI), in which R and R1 are defined as above, for example according to the method described by M. Fisher in *J. Med. Chem.* 1972, 15, 982.

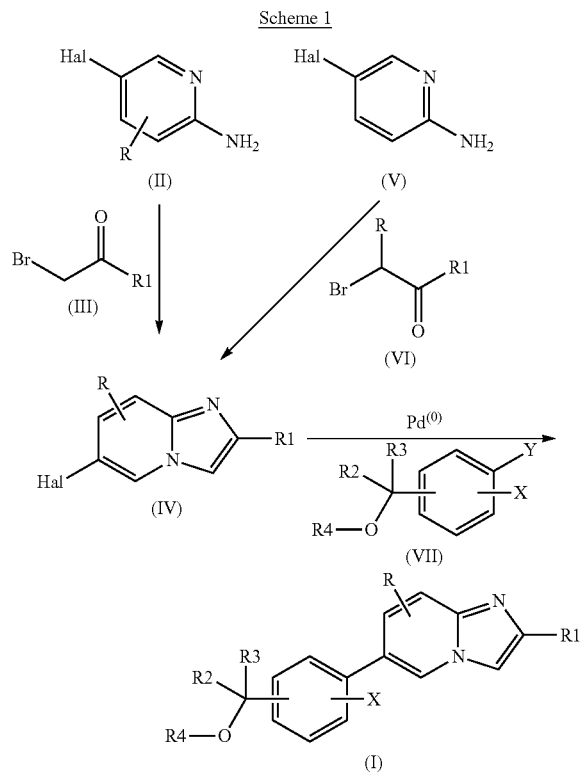

Scheme 1

In accordance with the invention, the compounds of general formula (I), in which R is at position 3 of the imidazopyridine nucleus and represents an alkyl group, can be prepared according to the process described in scheme 2.

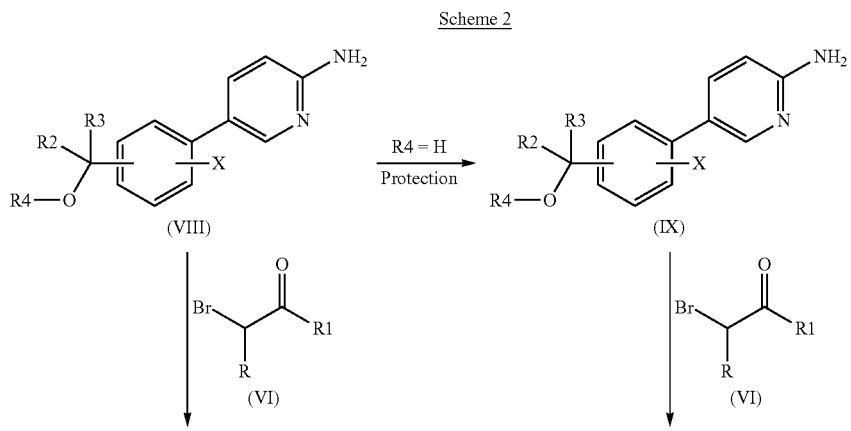

Scheme 2

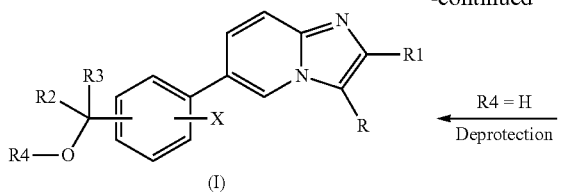

(I)

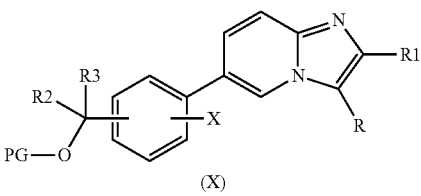

(X)

The compounds of the invention, in which R is at position 3 of the imidazopyridine nucleus, can be prepared according to scheme 2 by means of a condensation reaction between an aminopyridine of general formula (VIII), in which R2, R3, R4 and X are defined as above, R4 not being a hydrogen atom, and a bromoketone of general formula (VI), in which R1 is defined as above and R represents an alkyl group, for example according to the method described by M. Fisher in *J. Med. Chem.* 1972, 15, 982.

known to those skilled in the art. In particular, the aminopyridines of general formula (VIII) can be obtained according to methods known to those skilled in the art.

In accordance with the invention, the compounds of general formula (I), in which R is at position 3 of the imidazopyridine nucleus and represents a halogen atom, can be prepared according to the process described in scheme 3

Scheme 3

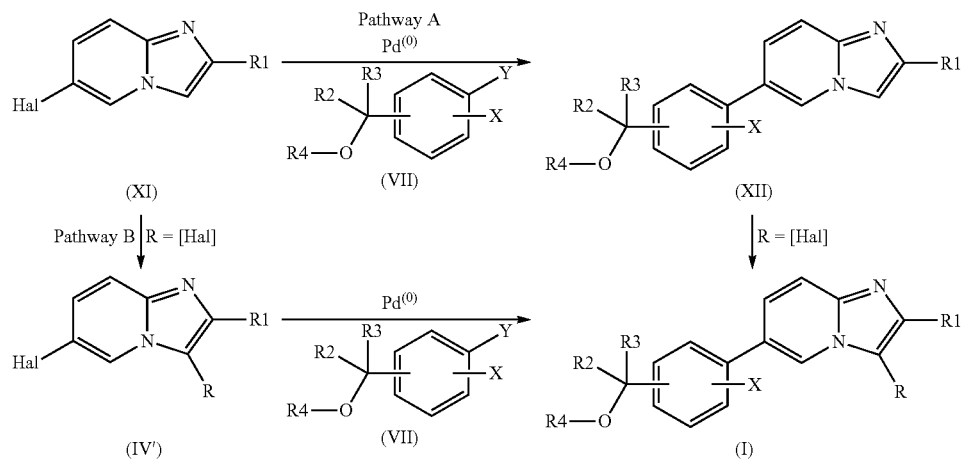

When R4 represents a hydrogen atom, the compounds of general formula (VIII) can be converted to compounds of general formula (IX), in which R2, R3 and X are defined as above, and PG represents a hydroxyl-functional-protecting group, as described, for example, by T. Greene in "*Protective Groups in Organic Synthesis*" (Wiley Interscience), for example a tert-butyldimethylsilyl group, by any method known to those skilled in the art. The compounds of general formula (VIII) are subjected to a condensation reaction with bromoketones of general formula (VI), in which R and R1 are defined as above, so as to obtain compounds of general formula (X), in which, R, R1, R2, R3 and X are defined as above and PG represents a hydroxyl-protecting group. Finally, the compounds of general formula (IX) are subjected to a deprotection reaction, as described, for example, by T. Greene in "*Protective Groups in Organic Synthesis*" (Wiley Interscience), so as to obtain the compounds of general formula (I), in which R is at position 3 of the imidazopyridine nucleus and R4 represents a hydrogen atom.

In scheme 2, the starting compounds and the reactants, when the method for preparing them is not described, are commercially available or described in the literature (for example, WO2004076412), or else can be prepared according to methods which are described therein and which are The compounds of the invention of general formula (I), in which X, R1, R2, R3 and R4 are defined as above and R is at position 3 of the imidazopyridine nucleus and represents a halogen, can be prepared according to scheme 3 pathway A by a reaction of halogenation of an imidazopyridine of general formula (XII), in which X, R1, R2, R3 and R4 are defined as above, by means of a halogenating agent such as N-chlorosuccinimide or of a fluorinating agent such as 1-chloromethyl-4-fluoro-1,4-diazoniabicyclo[2.2.2]octane bistetrafluoroborate, also known under the trade name "selectfluor". The compounds of general formula (XII) can be obtained by means of a coupling reaction, catalysed by a metal such as palladium, between an imidazopyridine of general formula (XI), in which R1 is defined as above and Hal represents a halogen atom, and a derivative of general formula (VII), in which R2, R3, R4 and X are defined as above and Y represents a boron or tin derivative, for example according to the method described by A. Gueiffier in *Helv. Chim. Acta* 2001, 84, 3610-3615.

Alternatively, the compounds of the invention of general formula (I), in which X, R1, R2, R3 and R4 are defined as above and R is at position 3 of the imidazopyridine nucleus and represents a halogen, can be prepared according to scheme 3 pathway B by means of a coupling reaction, catalysed by a metals such as palladium, between an imidazopyridine of general formula (IV'), in which R1 is defined as above, R represents a fluorine or chlorine atom and Hal represents a bromine or iodine atom, and a derivative of general formula (VII), in which R2, R3, R4 and X are defined as above and Y represents a boron or tin derivative, so as to obtain the compounds of general formula (I), for example according to the method described by A. Gueiffier in *Helv. Chim. Acta* 2001, 84, 3610-3615. The compounds of general formula (IV') can be obtained by halogenation of the imidazopyridines of formula (XI) by means of an agent such as N-chlorosuccinimide The products of formula (I), can be subjected, if desired and if necessary, to any reactions known to those skilled in the art, in any order, in order to be converted into other products of formula (I).

By way of examples of reactions, mention may be made of: reactions for esterification or amidation of an acid function, carbamoylation reactions, ester function hydrolysis reactions, reactions for conversion of a hydroxyl function to an alkoxy function, coupling reactions catalysed by a transition metal, reactions for protection of reactive functions, reactions for removal of the protective groups that protective reactive functions may bear, salification reactions with an inorganic or organic acid or with a base so as to obtain a corresponding salt, reactions for resolving racemic forms into enantiomers, said products of formula (I) thus obtained being, where appropriate, in all the possible racemic, enantiomeric and diastereoisomeric isomer forms.

According to another of its aspects, a subject of the invention is also the compounds of formulae (VIIIa), (VIIIb), (IXa), (IXb), (IXc) and (IV'a). These compounds are useful as synthesis intermediates for the compounds of formula (I).

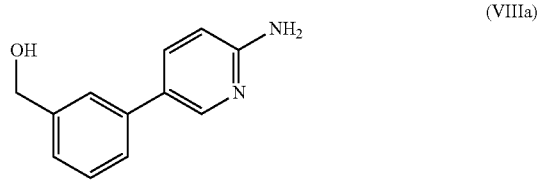

(VIIIa)

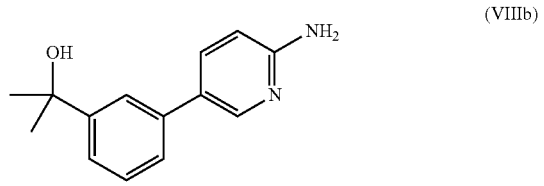

(VIIIb)

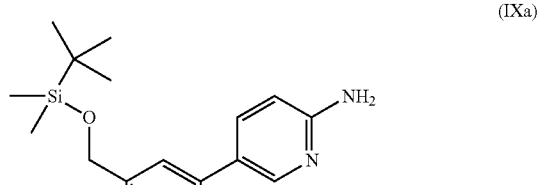

(IXa)

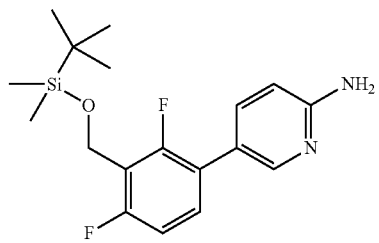

(IXb)

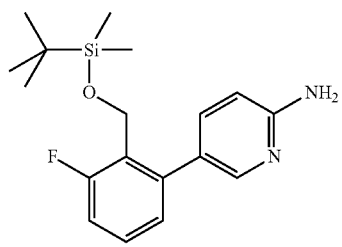

(IXc)

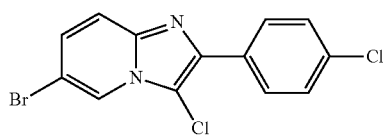

(IV'a)

The compound of formula (VIIIa) can be prepared by means of a coupling reaction, catalysed by a metal such as palladium, between 5-bromo-2-aminopyridine and a boronic acid derivative, for example 3-(hydroxymethyl)phenylboronic acid, as described in Example No. 3. The compound of formula (VIIIb) can be prepared by means of a coupling reaction, catalysed by a metal such as palladium, between 2-(3-bromophenyl)propan-2-ol and an aminopyridine substituted with a boron derivative, such as, for example, a 5-(4,4,5,5-tetramethyl-1,3,2-dioxaborolan-2-yl)pyridin-2-ylamine, as described in Example No. 4. The compound of formula (IXa) can be prepared through the action of (tert-butylchlorodimethyl)silane on the compound (VIIIa) in a solvent, for example tetrahydrofuran, in the presence of a base such as imidazole, as described in Example No. 3. The compounds of formulae (IXb) and (IXc) can be obtained by means of a coupling reaction, catalysed by a metal such as palladium, between an aminopyridine substituted with a boron derivative such as, for example, a 5-(4,4,5,5-tetramethyl-1,3,2-dioxaborolan-2-yl)pyridin-2-ylamine, and a (tert-butyldimethyloxy)methylbromobenzene derivative, as described in Example No. 5. The compound of formula (IV'a) can be obtained through reaction of a halogenating agent, such as N-chlorosuccinimide, on 6-bromo-2-(4-chlorophenyl)imidazo[1,2-α]pyridine, as described in Example No. 6.

The compounds of formulae (VIIIa), (VIIIb), (IXa), (IXb), (IXc) and (IV'a) were prepared in the form of a powder or an oil, in the form of a base. Table 1 gives some physicochemical data of these intermediates.

TABLE 1

| No. | $^1$H NMR (DMSO-d6, δ ppm); M + H; Mp |
|---|---|
| (VIIIa) | 4.55 (d, 2H); 5.2 (t, 1H); 6.05 (s, 2H); 6.55 (d, 1H); 7.2 (d, 1H); from 7.3 to 7.55 (m, 3H); 7.7 (d, 1H); 8.25 (s, 1H); M + H = 201 |
| (VIIIb) | 1.45 (s, 6H); 5.0 (s, 1H); 6.0 (s, 2H); 6.55 (d, 1H); from 7.3 to 7.4 (m, 3H); 7.65 (s, 1H); 7.7 (d, 1H); 8.25 (s, 1H). M + H = 229 |

TABLE 1-continued

| No. | $^1$H NMR (DMSO-d6, δ ppm); M + H; Mp |
|---|---|
| (IXa) | 0.09 (s, 6H); 0.91 (s, 9H); 4.75 (s, 2H); 6.02 (m, 2H); 6.52 (dd, 1H); 7.21 (d, 1H); 7.36 (t, 1H); 7.43 (d, 1H); 7.47 (s, 1H); 7.66 (dd, 1H); 8.21 (d, 1H). M + H = 315; Mp = 82-84° C. |
| (IXb) | 0 (s, 6H); 0.8 (s, 9H); 4.4 (s, 2H); 6.05 (s, 2H); 6.45 (d, 1H); 7.05 (t, 1H); from 7.35 to 7.45 (m, 2H); 8.0 (s, 1H). M + H = 351 |
| (IXc) | 0 (s, 6H); 0.85 (s, 9H); 4.5 (s, 2H); 6.05 (s, 2H); 6.45 (d, 1H); from 7.05 to 7.15 (m, 2H); from 7.3 to 7.4 (m, 1H); from 7.45 to 7.5 (m, 1H); 8.0 (d, 1H). M + H = 333 |
| (IV'a) | 7.55 (d, 1H); 7.6 (d, 2H); 7.7 (d, 1H); 8.15 (d, 2H) 8.7 (s, 1H) |

The following examples describe the preparation of some compounds in accordance with the invention. These examples are not limiting and merely illustrate the present invention. The numbers of the compounds exemplified refer back to those given in Table 2 hereinafter, which illustrates the chemical structures of some compounds according to the invention.

The nomenclature of the compounds was established on the basis of the Autonom software.

EXAMPLE 1

{3-[2-(4-Chlorophenyl)-8-methylimidazo[1,2-α] pyridin-6-yl]phenyl}ethanol (Compound 1 of the table)

1.1 6-Bromo-2-(4-chlorophenyl)-8-methylimidazo[1, 2-α]pyridine 1.70 g of 2-amino-5-bromo-3-methylpyridine and 2.13 g of 2-bromo-1-(4-chlorophenyl)ethanone in 75 ml of n-propanol are placed in a round-bottomed flask. 1.08 g of sodium hydrogen carbonate are added. The mixture is heated at 80° C. for 6 h. The reaction mixture is allowed to cool and the solvent is evaporated off under reduced pressure. The residue is taken up between dichloromethane and water, the organic phase is then separated and dried, and the filtrate is concentrated under reduced pressure. The residue is purified by silica gel chromatography, elution being carried out with a dichloromethane/methanol mixture. The solid obtained is triturated from diethyl ether and recovered by filtration. 1.7 g of compound are obtained.

$^1$H NMR (CDCl$_3$-d$_3$, δ in ppm): 2.6 (s, 3H); 7.0 (s, 1H); 7.4 (d, 2H); 7.7 (s, 1H); 7.9 (d, 2H); 8.1 (s, 1H). M+H=322.

1.2 {3-[2-(4-Chlorophenyl)-8-methylimidazo[1,2-α] pyridin-6-yl]phenyl}methanol 10.5 ml of acetonitrile, 10.5 ml of toluene and 8.5 ml of a 2M solution of sodium carbonate are placed in a round-bottomed flask, and the mixture is degassed with argon for 10 min. 704 mg of 6-bromo-2-(4-chlorophenyl)-8-methylimidazo[1,2-α]pyridine, 497 mg of 3-hydroxymethylphenylboronic acid and 126 mg of tetrakis(triphenylphosphine)palladium are added. The mixture is stirred for 5 h at 75° C. After cooling, the catalyst is removed by filtration and washed with ethyl acetate. The organic phase is separated and dried and the filtrate is concentrated under reduced pressure. The residue is purified by silica gel chromatography, elution being carried out with a dichloromethane/methanol mixture. The solid obtained is triturated from diethyl ether, recovered by filtration and then oven-dried under reduced pressure. 431 mg of compound are obtained.

Mp=174-177° C. $^1$H NMR (DMSO-d$_6$, δ in ppm): 2.6 (s, 3H); 4.6 (d, 2H); 5.3 (t, 1H); 7.3 (d, 1H); from 7.4 to 7.5 (m, 4H); 7.6 (d, 1H); 7.7 (s, 1H); 8.0 (d, 2H); 8.4 (s, 1H); 8.7 (s, 1H). M+H=349.

EXAMPLE 2

[3-(3-Methyl-2-phenylimidazo[1,2-α]pyridin-6-yl) phenyl]methanol (Compound 3 of the table)

2.1 6-Bromo-3-methyl-2-phenylimidazo[1,2-α]pyridine

In a 100 ml round-bottomed flask, 865 mg of 2-amino-5-bromopyridine are dissolved in 25 ml of acetone, then 1.06 g of 2-bromo-1-phenyl-1-propanone are added and the mixture is heated at the reflux of the solvent for 57 hours. The reaction mixture is allowed to cool and then the precipitate is recovered by filtration, washed with diethyl ether and dried under reduced pressure. 350 mg of compound are obtained.

$^1$H NMR (DMSO-d$_6$, δ in ppm): 2.82 (s, 3H); from 7.55 to 7.9 (m, 5H); 7.95 (d, 1H, J=4.2 Hz); 8.1 (d, 1H, J=4.2 Hz); 9.22 (s, 1H). M+H=287.

2.2 [3-(3-Methyl-2-phenylimidazo[1,2-α]pyridin-6-yl)phenyl]methanol 5 ml of acetonitrile, 5 ml of toluene and 5 ml of a 2M solution of sodium carbonate are placed in a round-bottomed flask, the mixture is degassed with argon for 15 min, and then 355 mg of 6-bromo-3-methyl-2-phenylimidazo[1,2-α]pyridine, 282 mg of 3-hydroxymethylphenylboronic acid and 71 mg of tetrakis(triphenylphosphine)palladium are added. The mixture is stirred for 16 h in a thermostated bath at 90° C. The reaction mixture is then cooled to ambient temperature and the solvents are evaporated off under reduced pressure. The residue is taken up with 30 ml of a 50/50 dichloromethane/methanol mixture. An insoluble material is removed by filtration through celite. The filtrate is evaporated under reduced pressure and the residue is purified by silica gel chromatography, elution being carried out with a dichloromethane/methanol mixture. The solid obtained is taken up with diethyl ether and recovered by filtration and then recrystallized from 20 ml of ethanol. 110 mg of compound are obtained.

Mp=222-223° C. $^1$H NMR (DMSO-d$_6$, δ in ppm): 2.75 (s, 3H); 4.6 (d, 2H); 5.25 (t, 1H); from 7.3 to 7.4 (m, 2H); from 7.45 to 7.55 (m, 3H); 7.6 (d, 1H); 7.7 (d, 2H); 7.75 (s, 1H); 7.85 (d, 2H); 8.5 (s, 1H). M+H=315.

EXAMPLE 3

{3-[2-(2,4-difluorophenyl)-3-methylimidazo[1,2-α] pyridin-6-yl]phenyl}-methanol hydrochloride (1:1) (compound 4 of the table)

3.1 [3-(6-Aminopyridin-3-yl)phenyl]methanol 2.0 g of tetrakis(triphenylphosphine)palladium and 75 ml of a 2M solution of sodium carbonate are added to a round-bottomed flask containing a solution of 5.0 g of 5-bromopyridin-2-ylamine in 140 ml of toluene, 5.7 g of 3-(hydroxymethyl)phenylboronic acid and 70 ml of ethanol degassed beforehand. The mixture is heated at 80° C. for 16 h. After cooling, the reaction mixture is concentrated under reduced pressure. The residue is taken up between water and ethyl acetate. The organic phase is separated, dried and concentrated under reduced pressure. The residue is purified by silica gel chromatography, elution being carried out with a dichloromethane/methanol mixture. 4.99 g of compound are obtained.

$^1$H NMR (DMSO-d$_6$, δ in ppm): 4.55 (d, 2H); 5.2 (t, 1H); 6.05 (s, 2H); 6.55 (d, 1H); 7.2 (d, 1H); from 7.3 to 7.55 (m, 3H); 7.7 (d, 1H); 8.25 (s, 1H); M+H=201.

3.2 5-[3-(tert-Butyldimethylsilanyloxymethyl)phenyl]pyridin-2-ylamine 4.99 g of [3-(6-aminopyridin-3-yl)phenyl]methanol are placed in a round-bottomed flask and dissolved in 240 ml of tetrahydrofuran. 2.2 g of 1H-imidazole are added thereto, followed by 4.51 g of tert-butylchlorodimethylsilane, and the mixture is left to stir at ambient temperature for 48 hours. The reaction mixture is then hydrolyzed with water and the organic phase, extracted with ethyl acetate, is separated, dried over magnesium sulphate and concentrated under reduced pressure. The residue obtained is purified by silica gel chromatography, elution being carried out with a heptane/ethyl acetate mixture. 7.0 g of compound are obtained.

$^1$H NMR (DMSO-d$_6$, δ in ppm): 0.09 (s, 6H); 0.91 (s, 9H); 4.75 (s, 2H); 6.02 (m, 2H); 6.52 (dd, 1H); 7.21 (d, 1H); 7.36 (t, 1H); 7.43 (d, 1H); 7.47 (s, 1H); 7.66 (dd, 1H); 8.21 (d, 1H). M+H=315; Mp=82-84° C.

3.3 6-[3-(tert-Butyldimethylsilanyloxymethyl)phenyl]-2-(2,4-difluorophenyl)-3-methylimidazo[1,2-α]pyridine 300 mg of 5-[3-(tert-butyldimethylsilanyloxymethyl)phenyl]pyridin-2-ylamine dissolved in 5 ml of ethanol are placed in a screw reactor. 200 mg of sodium hydrogen carbonate and 470 mg of 2-bromo-1-(2,4-difluorophenyl)propan-1-one are added thereto. The reactor is closed and heated at 80° C. for 20 h. After cooling, the reaction mixture is concentrated under reduced pressure. The residue obtained is purified by silica gel chromatography, elution being carried out with a heptane/ethyl acetate mixture. 220 mg of compound are obtained.

$^1$H NMR (CDCl$_3$, δ in ppm): 0 (s, 6H); 0.85 (s, 9H); 2.4 (s, 3H); 4.7 (s, 2H); from 6.75 to 6.95 (m, 2H); from 7.2 to 7.35 (m, 4H); 7.45 (s, 1H); from 7.55 to 7.65 (m, 2H); 7.95 (s, 1H). M+H=465.

3.4 {3-[2-(2,4-Difluorophenyl)-3-methylimidazo[1,2-α]pyridin-6-yl]phenyl}methanol 210 mg of 6-[3-(tert-butyldimethylsilanyloxymethyl)phenyl]-2-(2,4-difluorophenyl)-3-methylimidazo[1,2-α]pyridine in 5 ml of tetrahydrofuran are placed in a round-bottomed flask and 240 mg of tetrabutylammonium fluoride are added thereto. The mixture is stirred at ambient temperature for 48 h. The reaction mixture is then concentrated under reduced pressure. The residue is purified by silica gel chromatography, elution being carried out with a dichloromethane/methanol mixture. 130 mg of compound are obtained.

M+H=351.

3.5 {3-[2-(2,4-difluorophenyl)-3-methylimidazo[1,2-α]pyridin-6-yl]phenyl}methanol hydrochloride (1:1)

A solution of 130 mg of {3-[2-(2,4-difluorophenyl)-3-methylimidazo[1,2-α]pyridin-6-yl]phenyl}methanol in dichloromethane and methanol is passed through a frit and 3.7 ml of a 0.1N solution of hydrochloric acid in isopropanol are added to the filtrate. The reaction mixture is then concentrated under reduced pressure. The residue obtained is triturated from diethyl ether and recovered by filtration and then oven-dried under reduced pressure. 128 mg of compound are obtained.

Mp=246-249° C. $^1$H NMR (DMSO-d$_6$, δ in ppm): 2.65 (s, 3H); 4.65 (s, 2H); from 7.35 to 7.65 (m, 4H); from 7.75 to 7.85 (m, 3H); 8.05 (d, 1H); 8.25 (d, 1H); 8.95 (s, 1H). M+H=351.

EXAMPLE 4

2-{3-[2-(4-Chlorophenyl)-3-methylimidazo[1,2-α]pyridin-6-yl]phenyl}propan-2-ol (Compound 12 of the table)

4.1 2-(3-Bromophenyl)propan-2-ol

Under a stream of argon, 6.5 g of 3-bromoacetophenone are placed in a round-bottomed flask and dissolved in 544 ml of diethyl ether and 272 ml of tetrahydrofuran. The mixture is cooled at 0° C. using an ice bath, and 100 ml of a 1M solution of methylmagnesium bromide in dibutyl ether are added thereto, dropwise. The mixture is stirred at 0° C. for 1 h and 400 ml of a saturated aqueous solution of ammonium chloride are added. The organic phase is separated, dried over magnesium sulphate and concentrated under reduced pressure. 10.0 g of compound are obtained.

$^1$H NMR (DMSO-d$_6$, δ in ppm): 1.45 (s, 6H); 5.15 (s, 1H); 7.25 (t, 1H); 7.4 (d, 1H); 7.45 (d, 1H); 7.65 (s, 1H).

4.2 2-[3-(6-Aminopyridin-3-yl)phenyl]propan-2-ol

Under a stream of argon, 9.0 g of compound obtained in stage 4.1, 11.05 g of 5-(4,4,5,5-tetramethyl-1,3,2-dioxaborolan-2-yl)pyridin-2-ylamine, 83.7 ml of a 2M solution of sodium carbonate and 1.70 g of tetrakis(triphenylphosphine)palladium are placed in a round-bottomed flask, and dissolved in 523 ml of N,N-dimethylformamide. The mixture is heated for 1 h 30 at 80° C. After cooling to ambient temperature, 1 l of ethyl acetate is added to the reaction medium, and the mixture is filtered through celite. The organic phase is then separated, washed 3 times with a saturated solution of sodium chloride, dried over magnesium sulphate and concentrated under reduced pressure. The residue is purified by silica gel chromatography, elution being carried out with a dichloromethane/methanol mixture. The solid obtained is triturated from diisopropyl ether, recovered by filtration, and then oven-dried under reduced pressure. 2.35 g of compound are obtained.

$^1$H NMR (DMSO-d$_6$, δ in ppm): 1.45 (s, 6H); 5.0 (s, 1H); 6.0 (s, 2H); 6.55 (d, 1H); from 7.3 to 7.4 (m, 3H); 7.65 (s, 1H); 7.7 (d, 1H); 8.25 (s, 1H).

4.3 2-{3-[2-(4-Chlorophenyl)-3-methylimidazo[1,2-α]pyridin-6-yl]phenyl}propan-2-ol 58.8 mg (0.7 mmol) of sodium bicarbonate are weighed into a microwave tube. 57 mg (0.25 mmol) of the compound obtained in 4.2, in solution in 2 ml of propan-1-ol, are added thereto, followed by 92 mg (0.375 mmol) of 2-bromo-1-(4-chlorophenyl)propan-1-one in solution in 1 ml of propan-1-ol. The tube is sealed and then irradiated for 10 min at 180° C. The reaction mixture is cooled to ambient temperature, 200 mg of propanethiol supported on silica (Biotage Si-Thiol) are added thereto and the mixture is stirred for 6 h at ambient temperature and then filtered. The residue is washed with twice 2 ml of propan-1-ol, and the filtrate is then evaporated and purified by chromatography. 26.4 mg of compound are obtained.

$^1$H NMR (DMSO-$d_6$, δ in ppm): 1.5 (s, 6H); 2.75 (s, 3H); 5.1 (s, 1H); 7.45 (t, 1H); 7.5 (d, 1H); 7.55 (d, 2H); from 7.6 to 7.7 (m, 3H); from 7.8 to 7.9 (m, 3H); 8.6 (s, 1H). M+H=377.

EXAMPLE 5

[2,6-Difluoro-3-(3-methyl-2-phenylimidazo[1,2-α] pyridin-6-yl)phenyl]-methanol (Compound 17 of the table)

5.1 (3-Bromo-2,6-difluorophenyl)methanol 20 g of 3-bromo-2,6-difluorobenzaldehyde are dissolved in 450 ml of methanol and cooled in an ice bath; 3.42 g of sodium borohydride are then added thereto, portionwise. The mixture is stirred at ambient temperature for 1 hour and the solvent is then evaporated off under reduced pressure. The residue is taken up between water and dichloromethane, and the organic phase organic is separated, dried, and concentrated under reduced pressure. The residue is crystallized from n-pentane. 14.6 g of compound, used as it is in the subsequent stage, are obtained.

$^1$H NMR spectrum (CDCl$_3$, δ in ppm): 2.0 (s, 1H); 4.9 (s, 2H); from 6.85 to 7.0 (m, 1H); from 7.5 to 7.65 (m, 1H).

5.2 (3-Bromo-2,6-difluorobenzyloxy)-tert-butyldimethylsilane 11.15 g of the compound obtained in 5.1 are dissolved in 150 ml of THF, 5.1 g of imidazole and then 9.04 g of chloro-tert-butyldimethylsilane are added and the mixture is stirred at ambient temperature for 24 hours. The solvent is then evaporated off, the residue is taken up between water and diethyl ether, and the organic phase is separated by settling out, washed with water and dried over sodium sulphate. The solvent is evaporated off under reduced pressure. 17.5 g of oil are obtained.

$^1$H NMR spectrum (CDCl$_3$, δ in ppm): 0.0 (s, 6H); 0.8 (s, 9H); 4.65 (s, 2H); from 6.65 to 6.7 (m, 1H); from 7.3 to 7.4 (m, 1H).

5.3 5-[3-(tert-Butyldimethylsilanyloxymethyl)-2,4-difluorophenyl]pyridin-2-ylamine 6.7 g of the compound obtained in 5.2, 4.40 g of 5-(4,4,5,5-tetramethyl-1,3,2-dioxaborolan-2-yl)pyridin-2-ylamine, 30 ml of a 2M solution of sodium carbonate and 10.816 mg of [1,1'-bis(diphenylphosphino)ferrocene]dichloropalladium are dissolved in 80 ml of N,N-dimethylformamide and placed in a round-bottomed flask under a stream of argon. The mixture is heated for 2 h at 80° C. After cooling to ambient temperature, the solvents are evaporated off under reduced pressure and the residue is taken up between water and ethyl acetate and an insoluble material is removed by filtration through celite. The organic phase is separated by settling out, washed with a saturated aqueous solution of sodium chloride and dried over sodium sulphate. The compound is purified by chromatography, elution being carried out with a mixture of dichloromethane and methanol. 4.25 g of a white solid are obtained.

$^1$H NMR spectrum (DMSO-$d_6$, δ in ppm): 0 (s, 6H); 0.8 (s, 9H); 4.4 (s, 2H); 6.05 (s, 2H); 6.45 (d, 1H); 7.05 (t, 1H); from 7.35 to 7.45 (m, 2H); 8.0 (s, 1H). M+H=351

5.4 6-[3-(tert-Butyldimethylsilanyloxymethyl)-2,4-difluorophenyl]-3-methyl-2-phenylimidazo[1,2-α] pyridine By carrying out the process as in Example 4.3, starting from 0.25 mmol of the compound obtained in 5.3 and 0.375 mmol of 2-bromo-1-phenylpropan-1-one, the expected compound, used as it is for the subsequent stage, is obtained.

5.5 [2,6-Difluoro-3-(3-methyl-2-phenylimidazo[1,2-α]pyridin-6-yl)phenyl]methanol The crude compound obtained in 5.4 is dissolved in 5 ml of THF containing 0.5 mmol of tetrabutylammonium fluoride hydrate. The mixture is stirred for 16 h at ambient temperature and the solvent is then evaporated off under reduced pressure. The compound is purified by chromatography. 22 mg of compound are obtained.

$^1$H NMR (DMSO-$d_6$, δ in ppm): 2.7 (s, 3H); 4.6 (s, 2H); 5.35 (s, 1H); 7.25 (t, 1H); from 7.35 to 7.45 (m, 2H); 7.5 (t, 2H); from 7.65 to 7.7 (m, 2H); 7.85 (d, 2H); 8.45 (s, 1H). M+H=351.

EXAMPLE 6

2-{3-[3-Chloro-2-(4-chlorophenyl)imidazo[1,2-α] pyridin-6-yl]phenyl}propan-2-ol (Compound 23 of the table)

6.1 6-Bromo-2-(4-chlorophenyl)imidazo[1,2-α]pyridine 2.5 g (14.45 mmol) of 2-amino-5-bromopyridine, 3.37 g (14.45 mmol) of 2-bromo-4'-chloroacetophenone, 1.82 g (21.67 mmol) of sodium hydrogen carbonate and 110 ml of 1-propanol are introduced into a 250 ml three-necked flask, equipped with a magnetic stirrer and maintained under a nitrogen atmosphere. After stirring for 18 hours at 80° C., the reaction mixture is brought back to ambient temperature and diluted with 400 ml of water. The precipitate formed is recovered by filtration, washed with water, and then dried at 80° C. under reduced pressure. 3.96 g of expected product are thus isolated in the form of a beige powder.

Mp=210-211° C.

$^1$H NMR (DMSO D$_6$), δ (ppm): 7.4 (d, 1H); 7.5 (d, 2H); 7.6 (d, 1H); 8.0 (d, 2H); 8.4 (s, $^1$H); 8.95 (s, 1H).

6.2 6-Bromo-3-chloro-2-(4-chlorophenyl)imidazo[1,2-α]pyridine 0.52 g (3.90 mmol) of N-chlorosuccinimide is added to a suspension of 1.0 g (3.25 mmol) of compound obtained in stage 6.1, in 100 ml of methanol, maintained under an inert atmosphere. The reaction mixture is stirred at ambient temperature for 2 h. After this period of time, the precipitate formed is recovered by filtration, washed with methanol, and then dried at 80° C. under reduced pressure. 0.94 g of the expected product is isolated in the form of a beige powder.

Mp=183-185° C.

$^1$H NMR (DMSO D$_6$), δ (ppm): 7.55 (d, 1H); 7.6 (d, 2H); 7.7 (d, 1H); 8.15 (d, 2H) 8.7 (s, 1H).

6.3 1-{3-[3-Chloro-2-(4-chlorophenyl)imidazo[1,2-α]pyridin-6-yl]phenyl}ethanone 15 ml of acetonitrile, 15 ml of toluene and 15 ml of a 2M aqueous solution of sodium carbonate are introduced into a 100 ml three-necked flask, equipped with a magnetic stirrer and maintained under an inert atmosphere. 0.8 g (2.34 mmol) of compound obtained according to the protocol described in stage 6.2, 0.49 g (3.04 mmol) of 3-acetylphenylboronic acid and 130 mg (0.12 mmol) of tetrakis(triphenylphosphine)palladium are added to this solution. After stirring for 4 hours at 80° C., the reaction mixture, brought back to ambient temperature, is concentrated to one-third under reduced pressure, diluted with 100 ml of water and then extracted with three times 40 ml of ethyl acetate. The combined organic phases are washed with twice 30 ml of water, dried over sodium sulphate, filtered, and concentrated under reduced pressure. The resulting solid is purified by silica gel column chromatography, elution being carried out with a mixture of heptane and ethyl acetate. 0.69 g of the expected product is isolated.
Mp=186-188° C.
$^1$H NMR (DMSO D$_6$), δ (ppm): 2.7 (s, 3H); 7.6 (d, 2H); 7.7 (m, 1H); 7.85 (s, 2H); 8.05 (d, 1H); 8.15 (d, 1H); 8.2 (d, 2H); 8.35 (s, 1H); 8.7 (s, 1H).

6.4 2-{3-[3-Chloro-2-(4-chlorophenyl)imidazo[1,2-α]pyridin-6-yl]phenyl}propan-2-ol 0.4 g (1.05 mmol) of compound obtained in stage 6.3, dissolved in a mixture of 100 ml of anhydrous diethyl ether and 75 ml of anhydrous THF, is added to a 250 ml three-necked flask, pre-dried in an oven, equipped with a magnetic stirrer and maintained under an inert atmosphere. 1.05 ml (2.10 mmol) of a 2M solution of methylmagnesium bromide in diethyl ether are added, dropwise, to this solution cooled to 0° C. The reaction mixture is stirred at 0° C. for four hours and then hydrolyzed by adding, with vigorous stirring, 100 ml of a solution of ammonium chloride (30% aqueous). The product is extracted with three times 50 ml of ethyl acetate. The combined organic phases are washed with twice 20 ml of water, dried over sodium sulphate and concentrated under reduced pressure. The resulting product is purified by silica gel column chromatography, elution being carried out with a mixture of heptane and dichloromethane. 148 mg of the expected product are thus isolated.
Mp=172-173° C.
$^1$H NMR (DMSO D$_6$), δ (ppm): 1.45 (s, 6H); 5.05 (s, 1H); from 7.3 to 7.6 (m, 7H); 7.7 (m, 2H); 7.8 (s, 1H); 8.1 (d, 2H); 8.45 (s, 1H).

EXAMPLE 7

2-{3-[2-(4-Chlorophenyl)-3-fluoroimidazo[1,2-α]pyridin-6-yl]phenyl}-propan-2-ol (Compound 22 of the table)

7.1 1-{3-[2-(4-Chlorophenyl)imidazo[1,2-α]pyridin-6-yl]phenyl}ethanone

This compound was prepared according to a process similar to that described in stage 6.3, by reacting 5 g (16.26 mmol) of 6-bromo-2-(4-chlorophenyl)imidazo[1,2-a]pyridine, prepared according to the protocol described in stage 6.1, with 3.46 g (21.13 mmol) of 3-acetylphenylboronic acid, in the presence of a 2M aqueous solution of sodium carbonate (90 ml) and of 0.94 g (0.81 mmol) of tetrakis(triphenylphosphine)palladium in 180 ml of a mixture of acetonitrile and toluene (v/v). 5.37 g of expected product are obtained
Mp=173-175° C.

7.2 2-{3-[2-(4-Chlorophenyl)imidazo[1,2-α]pyridin-6-yl]phenyl}propan-2-ol

This compound was prepared according to a process similar to that described in stage 6.4, by reacting 2 g (5.77 mmol) of compound prepared according to the protocol described in stage 7.1 with 2.06 g (17.30 mmol) of a solution of methylmagnesium bromide at 0° C. in 250 ml of mixture of ethyl ether and tetrahydrofuran (v/v). 1.45 g of the expected product are obtained.
$^1$H NMR (DMSO D$_6$), δ (ppm): 1.45 (s, 6H); 5.1 (s, 1H); 7.35-7.7 (m, 7H); 7.8 (s, 1H); 8.0 (d, 2H); 8.45 (s, 1H), 8.85 (s, 1H).

7.3 2-{3-[2-(4-Chlorophenyl)-3-fluoroimidazo[1,2-α]pyridin-6-yl]phenyl}propan-2-ol 0.195 g (1.10 mmol) of 1-chloromethyl-4-fluoro-1,4-diazoniabicyclo[2.2.2]octane bistetrafluoroborate ("selectfluor") in solution in 10 ml of a mixture of THF/water (v/v) is added, dropwise (15 minutes), to a suspension, stirred at 0° C. under an inert atmosphere, of 0.4 g (1.10 mmol) of compound prepared in stage 7.2, in 40 ml of acetonitrile. After stirring for 18 hours at ambient temperature, the reaction mixture is concentrated under reduced pressure. The product obtained is purified by silica column chromatography, elution being carried out with a mixture of heptane and ethyl acetate. The solid obtained after evaporation of the solvent under reduced pressure is oven-dried at 80° C., so as to give 82 mg of the expected product.
Mp=174-175° C.
$^1$H NMR (DMSO D$_6$), δ (ppm): 1.45 (s, 6H); 5.1 (s, 1H); 7.4-7.7 (m, 7H); 7.9 (s, 1H); 8.0 (d, 2H); 8.6 (s, 1H).

EXAMPLE 8

{3-[3-Chloro-2-(4-chlorophenyl)imidazo[1,2-α]pyridin-6-yl]phenyl}-methanol (Compound 21 of the table)

8.1 {3-[2-(4-Chlorophenyl)imidazo[1,2-α]pyridin-6-yl]phenyl}methanol

Under a string of nitrogen, 210 mg of compound obtained in 6.1, 155 mg of 3-(hydroxymethyl)phenylboronic acid and 24 mg of tetrakis(triphenylphosphine)palladium are placed in a microwave tube containing 3 ml of toluene degassed beforehand under a stream of nitrogen, 3 ml of acetonitrile and 3 ml of a 2M solution of sodium carbonate. The tube is placed in a microwave device and irradiated at 150° C. for 15 min. The organic phase is separated and dried and the filtrate is concentrated under reduced pressure. The residue obtained is taken up with dichloromethane. The precipitate is recovered by filtration, washed with dichloromethane and dried in a desiccator under reduced pressure. 175 mg of compound are obtained.
Mp=181-182° C.
$^1$H NMR (DMSO-d$_6$, δ in ppm): 4.57 (d, J=5.5 Hz, 2H); 5.23 (t, J=5.6 Hz, 1H); from 7.28 to 7.71 (m, 8H); 7.97 (m, J=8.5 Hz, 2H); 8.41 (s, 1H); 8.84 (m, 1H). M+H=335.

8.2 {3-[3-Chloro-2-(4-chlorophenyl)imidazo[1,2-α]pyridin-6-yl]phenyl}methanol Compound No. 21 was prepared according to a process similar to that described in stage 6.2, by reacting 100 mg (0 3 mmol) of compound prepared according to the protocol described in stage 8.1 with 52 mg (0.39 mmol) of N-chlorosuccinimide in 5 ml of methanol. 75 mg of the expected product are obtained.
Mp: 195-197° C.

$^1$H NMR (DMSO D$_6$), δ (ppm): 4.6 (d, 2H); 5.25 (t, 1H); 7.4 (d, 1H); 7.5 (t, 1H); from 7.65 to 7.8 (m, 6H); 8.15 (m, 2H); 8.55 (s, 1H).

EXAMPLE 9

3-Chloro-6-(3-methoxymethylphenyl)-2-(4-chlorophenyl)imidazo[1,2-α]pyridine (Compound 28 of the table)

This compound was prepared according to a process similar to that described in stage 6.3, by reacting 0.4 g (1.17 mmol) of compound prepared according to the protocol described in stage 6.2 with 0.25 g (1.52 mmol) of 3-methoxymethylphenylboronic acid, in the presence of a 2M aqueous solution of sodium carbonate (10 ml) and of 67 mg (0.06 mmol) of tetrakis(triphenylphosphine)palladium in 20 ml of a mixture of acetonitrile and toluene (v/v). 0.31 g of the expected product is obtained after purification.

Mp: 120-122° C.
$^1$H NMR (DMSO D$_6$), δ (ppm): 3.4 (s, 3H); 4.5 (s, 2H); 7.4 (m, 1H); 7.55 (m, 1H); 7.65 (d, 2H); from 7.75 to 7.85 (m, 4H); 8.15 (d, 2H); 8.6 (s, 1H).

The tables which follow illustrate the chemical structures of general formula (I) (Table 2) and the physicochemical characteristics (Table 3) of some examples of compounds according to the invention. In these tables:

- the "position" column indicates the position "2, 3 or 4" of substitution of the group

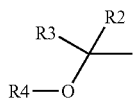

on the phenyl nucleus;
- "Ph" means phenyl;
- "Cl" means chlorine;
- "F" mean fluorine;
- "Me" means methyl;
- "MeO" means methoxy;
- "(F$_2$CH)O" means difluoromethoxy;
- in the R column, the number before the substituent indicates the position of substitution of the group R on the phenyl nucleus;
- in the column X, the number before the substituent indicates the position of substitution of group X on the imidazo[1,2-α]pyridine nucleus;
- in the "salt/base" column, "—" represents a compound in free base form, whereas "HCl" represents a compound in hydrochloride form and the ratio between parentheses is the (acid:base) ratio;
- the "Mp" column indicates the melting points of the products in degrees Celsius (° C.) or, when the products have been isolated in the form of an amorphous solid or of an oil, they are characterized by their mass [M+H].

TABLE 2

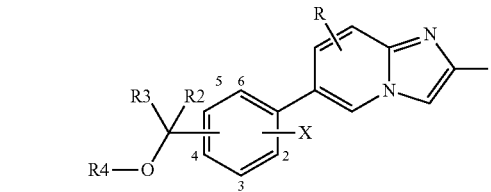

| Ex | R | R$_1$ | Position | X | R$_2$ | R$_3$ | R$_4$ | Salt/base |
|---|---|---|---|---|---|---|---|---|
| 1 | 8-Me | 4-Cl—Ph | 3 | H | H | H | H | — |
| 2 | 7-Me | 4-Cl—Ph | 3 | H | H | H | H | — |
| 3 | 3-Me | Ph | 3 | H | H | H | H | — |
| 4 | 3-Me | 2,4-(F)$_2$—Ph | 3 | H | H | H | H | HCl (1:1) |
| 5 | 3-Me | 3-Me-4-Cl—Ph | 3 | H | H | H | H | HCl (1:1) |
| 6 | 3-Me | 4-Cl—Ph | 3 | H | H | H | H | HCl (1:1) |
| 7 | 3-Me | 4-MeO—Ph | 3 | H | H | H | H | HCl (1:1) |
| 8 | 3-Me | 4-(F$_2$CH)O—Ph | 3 | H | H | H | H | HCl (1:1) |
| 9 | 8-Me | 2-Naphthyl | 3 | H | H | H | H | — |
| 10 | 8-Me | 2-Naphthyl | 4 | H | H | H | H | — |
| 11 | 3-Me | Ph | 3 | H | Me | Me | H | — |
| 12 | 3-Me | 4-Cl—Ph | 3 | H | Me | Me | H | — |
| 13 | 3-Me | 3-Cl—Ph | 3 | H | Me | Me | H | — |
| 14 | 3-Me | 2,4-diF—Ph | 3 | H | Me | Me | H | — |
| 15 | 3-Me | 4-MeO—Ph | 3 | H | Me | Me | H | — |
| 16 | 3-Me | 4-MeO—Ph | 2 | 3-F | H | H | H | — |
| 17 | 3-Me | Ph | 3 | 2,4-diF | H | H | H | — |
| 18 | 3-Me | 4-Cl—Ph | 3 | 2,4-diF | H | H | H | — |
| 19 | 3-Me | 3-Cl—Ph | 3 | 2,4-diF | H | H | H | — |
| 20 | 3-Me | 4-MeO—Ph | 3 | 2,4-diF | H | H | H | — |
| 21 | 3-Cl | 4-Cl—Ph | 3 | H | H | H | H | — |
| 22 | 3-F | 4-Cl—Ph | 3 | H | Me | Me | H | — |
| 23 | 3-Cl | 4-Cl—Ph | 3 | H | Me | Me | H | — |
| 24 | 3-Me | Ph | 2 | 3-F | H | H | H | — |
| 25 | 3-Me | 4-Cl—Ph | 2 | 3-F | H | H | H | — |
| 26 | 3-Me | 3-Cl—Ph | 2 | 3-F | H | H | H | — |
| 27 | 3-Me | 2,4-diF | 2 | 3-F | H | H | H | — |
| 28 | 3-Cl | 4-Cl—Ph | 3 | H | H | H | Me | — |
| 29 | 3-Cl | 4-Cl—Ph | 3 | 2,4-diF | H | H | H | — |

TABLE 3

| Ex NMR | $^1$H NMR spectra (DMSO-d6, δ in ppm) | Mp/[M + H] |
|---|---|---|
| 1 | 2.6 (s, 3H); 4.6 (d, 2H); 5.3 (t, 1H); 7.3 (d, 1H); de 7.4 to 7.5 (m, 4H); 7.6 (d, 1H); 7.7 (s, 1H); 8.0 (d, 2H); 8.4 (s, 1H); 8.7 (s, 1H). | 174-177 |
| 2 | 2.25 (s, 3H); 4.55 (d, 2H); 5.25 (t, 1H); 7.3 (d, 1H); de 7.35 to 7.55 (m, 6H); 8.0 (d, 2H); 8.35 (s, 1H); 8.4 (s, 1H). | 183-184 |
| 3 | 2.75 (s, 3H); 4.6 (d, 2H); 5.25 (t, 1H); de 7.3 to 7.4 (m, 2H); de 7.45 to 7.55 (m, 3H); 7.6 (d, 1H); 7.7 (d, 2H); 7.75 (s, 1H); 7.85 (d, 2H); 8.5 (s, 1H). | 222-223 |
| 4 | 2.65 (s, 3H); 4.65 (s, 2H); de 7.35 to 7.65 (m, 4H); de 7.75 to 7.85 (m, 3H); 8.05 (d, 1H); 8.25 (d, 1H); 8.95 (s, 1H). | 246-249 |
| 5 | 2.5 (s, 3H); 2.8 (s, 3H); 4.65 (s, 2H); 7.45 (d, 1H); 7.55 (t, 1H); from 7.65 to 7.75 (m, 2H); 7.8 (d, 1H); 7.85 (m, 2H); 8.05 (d, 1H); 8.25 (d, 1H); 9.0 (s, 1H); predominant isomer at 80% (the minority isomer at 20% being the 3-Cl-4-Me derivative) | 272-275 |
| 6 | 2.8 (s, 3H); 4.65 (s, 2H); 7.45 (d, 1H); 7.55 (t, 1H); from 7.7 to 7.8 (m, 3H); from 7.82 to 7.9 (m, 3H); 8.05 (d, 1H); 8.25 (d, 1H); 9.0 (s, 1H). | 263-267 |

TABLE 3-continued

| Ex | NMR $^1$H NMR spectra (DMSO-d6, δ in ppm) | Mp/[M + H] |
|---|---|---|
| 7 | 2.8 (s, 3H); 3.9 (s, 3H); 4.65 (s, 2H); 7.2 (m, 2H); 7.45 (d, 1H); 7.55 (t, 1H); 7.8 (m, 3H); 7.85 (s, 1H); 8.05 (d, 1H); 8.25 (d, 1H); 9.0 (s, 1H). | 260-263 |
| 8 | 2.9 (s, 3H); 4.7 (s, 2H); 7.3 (s, 1H); from 7.5 to 7.6 (m, 3H); 7.65 (m, 1H); 7.85 (d, 1H); 7.95 (s, 1H); 8.0 (d, 2H); 8.15 (d, 1H); 8.35 (d, 1H); 9.05 (s, 1H). | 259-261 |
| 9 | 2.65 (s, 3H); 4.6 (d, 2H); 5.2 (t, 1H); from 7.25 to 7.7 (m, 7H); from 7.85 to 8.15 (m, 4H); 8.5 (m, 2H); 8.75 (s, 1H). | 94-96 |
| 10 | 2.6 (s, 3H); 4.55 (d, 2H); 5.2 (t, 1H); from 7.4 to 7.6 (m, 5H); 7.65 (d, 2H); from 7.85 to 8.05 (m, 3H); 8.1 (d, 1H); 8.5 (s, 1H); 8.55 (s, 1H); 8.7 (s, 1H). | 198-200 |
| 11 | 1.5 (s, 6H); 2.75 (s, 3H); 5.1 (s, 1H); from 7.4 to 7.55 (m, 5H); 7.65 (d, 1H); 7.75 (s, 2H); from 7.8 to 7.9 (m, 3H); 8.6 (s, 1H). | [343] |
| 12 | 1.5 (s, 6H); 2.75 (s, 3H); 5.1 (s, 1H); 7.45 (t, 1H); 7.5 (d, 1H); 7.55 (d, 2H); from 7.6 to 7.7 (m, 3H); from 7.8 to 7.9 (m, 3H); 8.6 (s, 1H). | [377] |
| 13 | 1.5 (s, 6H); 2.75 (s, 3H); 5.1 (s, 1H); from 7.4 to 7.55 (m, 4H); from 7.6 to 7.65 (m, 3H); 7.8 (d, 1H); 7.9 (d, 2H); 8.55 (s, 1H). | [377] |
| 14 | 1.5 (s, 6H); 2.55 (s, 3H); 5.1 (s, 1H); from 7.2 to 7.25 (m, 1H); from 7.35 to 7.55 (m, 3H); from 7.6 to 7.75 (m, 4H); 7.85 (t, 1H); 8.5 (s, 1H). | [379] |
| 15 | 1.5 (s, 6H); 2.75 (s, 3H); 3.85 (s, 3H); 5.1 (s, 1H); 7.15 (m, 2H); 7.45 (t, 1H); 7.55 (d, 1H); 7.65 (d, 1H); from 7.75 to 7.9 (m, 5H); 8.65 (s, 1H). | [373] |
| 16 | 2.65 (s, 3H); 3.8 (s, 3H); 4.45 (s, 2H); 5.35 (s, 1H); 7.05 (d, 2H); from 7.25 to 7.35 (m, 2H); 7.4 (d, 1H); from 7.45 to 7.5 (m, 1H); 7.55 (d, 1H); 7.75 (d, 2H); 8.45 (s, 1H). | [363] |
| 17 | 2.7 (s, 3H); 4.6 (s, 2H); 5.35 (s, 1H); 7.25 (t, 1H); from 7.35 to 7.45 (m, 2H); 7.5 (t, 2H); from 7.65 to 7.7 (m, 2H); 7.85 (d, 2H); 8.45 (s, 1H). | [351] |
| 18 | 2.7 (s, 3H); 4.6 (s, 2H); 5.35 (s, 1H); 7.25 (t, 1H); 7.4 (d, 1H); 7.55 (d, 2H); from 7.65 to 7.7 (m, 2H); 7.85 (d, 2H); 8.5 (s, 1H). | [385] |
| 19 | 2.7 (s, 3H); 4.6 (s, 2H); 5.35 (s, 1H); 7.25 (t, 1H); 7.4 (d, 2H); 7.5 (t, 1H); from 7.65 to 7.7 (m, 2H); 7.8 (d, 1H); 7.85 (s, 1H); 8.5 (s, 1H). | [385] |
| 20 | 2.65 (s, 3H); 3.8 (s, 3H); 4.6 (s, 2H); 5.35 (s, 1H); 7.05 (d, 2H); 7.25 (t, 1H); 7.4 (d, 1H); from 7.6 to 7.7 (m, 2H); 7.75 (d, 2H); 8.45 (s, 1H). | [381] |
| 21 | 4.6 (d, 2H); 5.25 (t, 1H); 7.4 (d, 1H); 7.5 (t, 1H); from 7.65 to 7.8 (m, 6H); 8.15 (m, 2H); 8.55 (s, 1H). | 195-197 |
| 22 | 1.45 (s, 6H); 5.1 (s, 1H);. from 7.4 to 7.7 (m, 7H); 7.9 (s, 1H); 8.0 (d, 2H); 8.6 (s, 1H). | 174-175 |
| 23 | 1.45 (s, 6H); 5.05 (s, 1H);. from 7.3 to 7.6 (m, 7H); 7.7 (m, 2H); 7.8 (s, 1H); 8.1 (d, 2H); 8.45 (s, 1H). | 172-173 |
| 24 | 2.7 (s, 3H); 4.45 (d, 2H); 5.35 (t, 1H); from 7.25 to 7.55 (m, 7H); 7.65 (d, 1H); 7.85 (d, 2H); 8.5 (s, 1H). | [333] |
| 25 | 2.65 (s, 3H); 4.45 (d, 2H); 5.35 (t, 1H); from 7.25 to 7.35 (m, 2H); from 7.45 to 7.6 (m, 4H); 7.65 (d, 1H); 7.85 (d, 2H); 8.5 (s, 1H). | [367] |
| 26 | 2.7 (s, 3H); 4.45 (d, 2H); 5.35 (t, 1H); from 7.25 to 7.35 (m, 2H); from 7.4 to 7.55 (m, 4H); 7.7 (d, 1H); 7.8 (d, 1H); 7.85 (s, 1H); 8.5 (s, 1H). | [367] |
| 27 | 2.55 (s, 3H); 4.45 (d, 2H); 5.35 (t, 1H); from 7.2 to 7.55 (m, 6H); from 7.65 to 7.8 (m, 2H); 8.5 (s, 1H). | [369] |
| 28 | 3.4 (s, 3H); 4.5 (s, 2H); 7.4 (m, 1H); 7.55 (m, 1H); 7.65 (d, 2H); from 7.75 to 7.85 (m, 4H); 8.15 (d, 2H); 8.6 (s, 1H). | 120-122 |
| 29 | 4.1 (d, 2H); 5.35 (t, 1H); 7.25 (m, 1H); 7.55 (m, 3H); 7.7 (m, 1H); 7.85 (d, 1H); 8.15 (d, 2H); 8.5 (s, 1H). | 201-203 |

The compounds according to the invention were the subject of pharmacological tests for determining their modulatory effect on NOT.

Evaluation of the In Vitro Activity on N2A Cells

The activity of the compounds according to the invention was evaluated on a cell line (N2A) endogenously expressing the mouse Nurr1 receptor and stably transfected with the NOT binding response element (NBRE) coupled to the luciferase reporter gene. The $EC_{50}$ values are between 0.01 and 10 µM. The tests were carried out according to the procedure described below.

The Neuro-2A cell line comes from a standard commercial source (ATCC). The Neuro-2A clone was obtained from a spontaneous tumour originating from a mouse A albino strain by R. J. Klebe et al. This Neuro-2A line is subsequently stably transfected with 8NBRE-luciferase. The N2A-8NBRE cells are cultured to confluence in 75 cm$^2$ culture flasks containing DMEM supplemented with 10% of foetal calf serum, 4.5 g/l of glucose and 0.4 mg/ml of geneticin. After one week of culture, the cells are recovered with 0.25% trypsin for 30 seconds and then resuspended in DMEM without phenol red, containing 4.5 g/l of glucose, 10% of Hyclone defatted serum, and deposited in white, transparent-bottom, 96-well plates. The cells are deposited at a rate of 60 000 per well in 75 µl for 24 hours before the addition of the products. The products were applied in 25 µl and incubated for a further 24 hours. On the day of measurement, an equivalent volume (100 µl) of Steadylite is added to each well, followed by a waiting period of 30 minutes in order to obtain complete lysis of the cells and maximum production of the signal. The plates are then measured in a microplate luminescence counter after having been sealed with an adhesive film. The products are prepared in the form of a stock solution at $10^{-2}$ M, and then diluted in 100% of DMSO. Each product concentration is diluted beforehand in culture medium before incubation with the cells thus containing a final concentration of 0.625% of DMSO.

For example, compounds No. 1, 3, 10, 15 and 19 showed an $EC_{50}$ of 5; 0.5; 68; 161 and 1.7 nMm respectively. It therefore appears that the compounds according to the invention have a NOT-modulating effect.

The compounds according to the invention can therefore be used for the preparation of medicaments for their therapeutic use in the treatment or prevention of diseases involving NOT receptors.

Thus, according to another of its aspects, a subject of the invention is medicaments which comprise a compound of formula (I), or an addition salt of the latter with a pharmaceutically acceptable acid.

These medicaments are of use in therapeutics, in particular in the treatment and prevention of neurodegenerative diseases such as, for example, Parkinson's disease, Alzheimer disease, tauopathies (for example, progressive supranuclear palsy, frontotemporal dementia, corticobasal degeneration, Pick's disease); cerebral traumas such as ischemia and cranial traumas and epilepsy; psychiatric diseases such as schizophrenia, depression, substance dependence, attention deficit hyperactivity disorders; inflammatory diseases of the central nervous system, such as multiple sclerosis, encephalitis, myelitis and encephalomyelitis and other inflammatory diseases such as vascular pathologies, atherosclerosis, joint inflammations, arthritis, rheumatoid arthritis; osteoarthritis, Crohn's disease, ulcerative colitis; allergic inflammatory diseases such as asthma, autoimmune diseases such as type 1 diabetes, lupus, scleroderma, Guillain-Barré syndrome, Addison's disease and other immunomediated diseases; osteoporosis; cancers.

These compounds could also be used as a treatment combined with stem cell transplantations and/or grafts.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or salt thereof, may be administered in unit administration form, as a mixture with conventional pharmaceutical excipients, to animals and to humans for the prophylaxis or treatment of the disorders or the diseases above.

The suitable unit administration forms comprise oral administration forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

There may be particular cases where higher or lower dosages are appropriate; such dosages do not depart from the context of the invention. According to the usual practice, the dosage appropriate for each patient is determined by the physician according to the method of administration and the weight and response of said patient.

According to another of its aspects, the present invention also relates to a method for treating the pathologies indicated above, which comprises the administration, to a patient, of an effective dose of a compound according to the invention, or a pharmaceutically acceptable salt thereof.

What is claimed is:
1. A compound of formula (I):

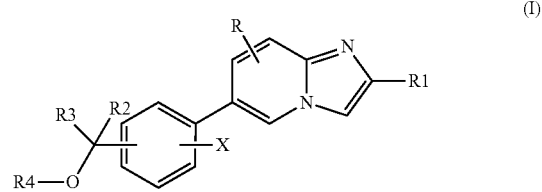

(I)

wherein:
$R_1$ represents a phenyl group or a naphthyl group, wherein these two groups are optionally substituted with one or more atoms or groups chosen, independently of one another, from the following atoms or groups: halogen, $(C_1-C_{10})$alkyl, halo$(C_1-C_{10})$alkyl, $(C_1-C_{10})$alkoxy, halo$(C_1-C_{10})$alkoxy, $(C_1-C_{10})$thioalkyl, —S(O)$(C_1-C_{10})$alkyl, —S(O)$_2$$(C_1-C_{10}$-alkyl), hydroxyl, cyano, nitro, hydroxy$(C_1-C_{10})$alkylene, NRaRb$(C_1-C_{10})$alkylene, $(C_1-C_{10})$alkoxy$(C_1-C_{10})$alkylenoxy, NRaRb, CONRaRb, SO$_2$NRaRb, NRcCORd, OC(O)NRaRb, OCO$(C_1-C_{10})$alkyl, NRcC(O)ORe, NRcSO$_2$Re, aryl$(C_1-C_{10})$alkylene, monocyclic heteroaryl and aryl, wherein the monocyclic heteroaryl or aryl are optionally substituted with one or more substituents chosen from a halogen, and a $(C_1-C_{10})$ alkyl, halo $(C_1-C_{10})$alkyl, $(C_1-C_{10})$alkoxy, halo$(C_1-C_{10})$alkoxy, NRaRb, hydroxyl, oxo, nitro, cyano or OCO$(C_1-C_{10})$alkyl group;

X represents from 1 to 4 substituents, which are identical to or different from one another, chosen from hydrogen, halogen, $(C_1-C_{10})$alkyl, $(C_1-C_{10})$alkoxy, NRaRb, cyano and nitro, wherein the $(C_1-C_{10})$alkyl is optionally substituted with one or more groups chosen from a halogen, $(C_1-C_{10})$alkoxy, halo$(C_1-C_{10})$alkoxy, NRaRb or hydroxyl;

R represents, at position 3, 5, 7 or 8 of the imidazo[1,2-a]pyridine, from 1 to 4 substituents, which are identical to or different from one another, chosen from a halogen, $(C_1-C_{10})$alkyl, halo$(C_1-C_{10})$alkyl and $(C_1-C_{10})$alkoxy;

$R_2$ and $R_3$ represent, independently of one another,
  a hydrogen atom;
  a $(C_1-C_{10})$alkyl group, optionally substituted with an Rf group; or
  an aryl group, optionally substituted with one or more substituents chosen from a halogen, and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro or cyano group;

$R_2$ and X can form, together with the carbon atoms which bear them, a carbon-based ring containing from 5 to 7 carbon atoms;

$R_4$ represents:
  a hydrogen atom;
  a $(C_1-C_{10})$alkyl group, optionally substituted with an Rf group; or
  an aryl group, optionally substituted with one or more substituents chosen from a halogen, and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro, cyano, $(C_1-C_{10})$alkyl(CO)—, CONRaRb, NRcCORd, OC(O)NRaRb, OCO$(C_1-C_{10})$alkyl, NRcC(O)ORe or aryl group, the aryl being optionally substituted with one or more substituents chosen from a halogen, and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro or cyano group;

Ra and Rb represent, independently of one another, a hydrogen atom or a $(C_1-C_{10})$alkyl, aryl$(C_1-C_{10})$alkylene or aryl group;

or Ra and Rb form, together with the nitrogen atom which bears them, an azetidine, pyrrolidine, piperidine, azepine, morpholine, thiomorpholine, piperazine or homopiperazine group, this group being optionally substituted with a $(C_1-C_{10})$alkyl, aryl or aryl$(C_1-C_{10})$alkylene group;

Rc and Rd represent, independently of one another, a hydrogen atom or a $(C_1-C_{10})$alkyl, aryl$(C_1-C_{10})$alkylene or aryl group, or Rc and Rd together form a $(C_2-C_5)$alkylene group;

Re represents a $(C_1-C_{10})$alkyl, aryl$(C_1-C_{10})$alkylene or aryl group, or Rc and Re together form a $(C_2-C_5)$alkylene group; and Rf represents a halogen atom, or a $(C_1-C_{10})$alkoxy, halo$(C_1-C_{10})$alkoxy, hydroxyl, cyano, NRaRb, C(O)NRaRb, NRcCORd, OC(O)NRaRb, OCO$(C_1-C_{10})$alkyl, NRcCOORe, SO$_2$NRaRb, NRcSO$_2$Re, aryl $(C_1-C_{10})$alkylene or aryl group, wherein the aryl is optionally substituted with one or more substituents chosen from a halogen, and a $(C_1-C_{10})$alkyl, halo$(C_1-C_{10})$alkyl, $(C_1-C_{10})$alkoxy, halo$(C_1-C_{10})$alkoxy, NRaRb, hydroxyl, nitro, cyano or OCO$(C_1-C_{10})$alkyl group;

or an acid addition salt thereof.

2. The compound of formula (I) according to claim 1, wherein:
  $R_1$ represents a phenyl group or a naphthyl group, optionally substituted with one or more atoms or groups chosen, independently of one another, from halogen atoms or $(C_1-C_{10})$ alkyl, $(C_1-C_{10})$ alkoxy and halo $(C_1-C_{10})$ alkoxy groups;
or an acid addition salt thereof.

3. The compound of formula (I) according to claim 1, wherein:
  X represents 1 or 2 substituent(s), which are identical to or different from one another, chosen from hydrogen and halogen atoms;
or an acid addition salt thereof.

4. The compound of formula (I) according to claim 1, wherein:
  R represents, at position 3, 7 or 8 of the imidazo[1,2-a]pyridine, 1 or 2 substituent(s), which are identical to or different from one another, chosen from halogen atoms and $(C_1-C_{10})$alkyl groups;
or an acid addition salt thereof.

5. The compound of formula (I) according to claim 1, wherein:
  $R_2$ and $R_3$ represent, independently of one another, a hydrogen atom or a $(C_1-C_{10})$alkyl group;
or an acid addition salt thereof.

6. The compound of formula (I) according to claim 1, wherein:
  $R_4$ represents a hydrogen atom or a $(C_1-C_{10})$alkyl group;
or an acid addition salt thereof.

7. The compound of formula (I) according to claim 1, wherein:
  the group

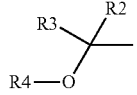

is at position 2, 3 or 4 on the phenyl nucleus which bears it;
or an acid addition salt thereof.

8. The compound of formula (I) according to claim 1, wherein:
  $R_1$ represents a phenyl group or a naphthyl group, optionally substituted with one or more atoms or groups chosen, independently of one another, from halogen atoms or $(C_1-C_{10})$alkyl, $(C_1-C_{10})$ alkoxy or halo $(C_1-C_{10})$ alkoxy groups;
  X represents 1 or 2 substituent(s), which may be identical to or different from one another, chosen from hydrogen and halogen atoms;
  R represents, at position 3, 7 or 8 of the imidazo[1,2-a]pyridine, a substituent chosen from halogen atoms and $(C_1-C_{10})$alkyl groups;
  $R_2$ and $R_3$ represent, independently of one another, a hydrogen atom or a $(C_1-C_{10})$alkyl group;
  $R_4$ represents a hydrogen atom or a $(C_1-C_{10})$alkyl group; and
  the group

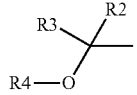

is at position 2, 3 or 4 on the phenyl nucleus which bears it; or an acid addition salt thereof.

9. The compound of formula (I) according to claim 1, wherein:
  $R_1$ represents a phenyl group or a naphthyl group, wherein these two groups are optionally substituted with one or more atoms or groups chosen, independently of one another, from the following atoms or groups: halogen, $(C_1-C_{10})$alkyl, $(C_1-C_{10})$alkoxy and halo$(C_1-C_{10})$alkoxy;

X represents a hydrogen atom,

R is at position 3, 7 or 8 of the imidazo[1,2-a]pyridine and represents a $(C_1-C_{10})$alkyl;

$R_2$ and $R_3$ represent, independently of one another, a hydrogen atom; and $R_4$ represents a hydrogen atom;

or an acid addition salt thereof.

10. A compound selected from the group consisting of:
{3-[2-(4-chlorophenyl)-8-methylimidazo[1,2-a]pyridin-6-yl]phenyl}methanol;
{3-[2-(4-chlorophenyl)-7-methylimidazo[1,2-a]pyridin-6-yl]phenyl}methanol;
[3-(3-methyl-2-phenylimidazo[1,2-a]pyridin-6-yl)phenyl]methanol;
{3-[2-(2,4-difluorophenyl)-3-methylimidazo[1,2-a]pyridin-6-yl]phenyl}methanol and the hydrochloride thereof;
{3-[2-(4-chloro-3-methylphenyl)-3-methylimidazo[1,2-a]pyridin-6-yl]phenyl}methanol and the hydrochloride thereof;
{3-[2-(4-chlorophenyl)-3-methylimidazo[1,2-a]pyridin-6-yl]phenyl}methanol and the hydrochloride thereof;
{3-[2-(4-methoxyphenyl)-3-methylimidazo[1,2-a]pyridin-6-yl]phenyl}methanol and the hydrochloride thereof;
{3-[2-[4-(difluoromethyloxy)phenyl]-3-methylimidazo[1,2-a]pyridin-6-yl]phenyl}methanol and the hydrochloride thereof;
[3-(8-methyl-2-naphthyl-2-ylimidazo[1,2-a]pyridin-6-yl)phenyl]methanol;
[4-(8-methyl-2-naphthyl-2-ylimidazo[1,2-a]pyridin-6-yl)phenyl]methanol;
2-[3-(3-methyl-2-phenylimidazo[1,2-a]pyridin-6-yl)phenyl]propan-2-ol;
2-{3-[2-(4-chlorophenyl)-3-methylimidazo[1,2-a]pyridin-6-yl]phenyl}propan-2-ol;
2-{3-[2-(3-chlorophenyl)-3-methylimidazo[1,2-a]pyridin-6-yl]phenyl}propan-2-ol;
2-{3-[2-(2,4-difluorophenyl)-3-methylimidazo[1,2-a]pyridin-6-yl]phenyl}propan-2-ol;
2-{3-[2-(4-methoxyphenyl)-3-methylimidazo[1,2-a]pyridin-6-yl]phenyl}propan-2-ol;
{2-fluoro-6-[2-(4-methoxyphenyl)-3-methylimidazo[1,2-a]pyridin-6-yl]phenyl}methanol;
[2,6-difluoro-3-(3-methyl-2-phenylimidazo[1,2-a]pyridin-6-yl)phenyl]methanol;
{3-[2-(4-chlorophenyl)-3-methylimidazo[1,2-a]pyridin-6-yl]-2,6-difluorophenyl}methanol;
{3-[2-(3-chlorophenyl)-3-methylimidazo[1,2-c]pyridin-6-yl]-2,6-difluorophenyl}methanol;
{2,6-difluoro-3-[2-(4-methoxyphenyl)-3-methylimidazo[1,2-c]pyridin-6-yl]-phenyl}methanol;
{3-[3-chloro-2-(4-chlorophenyl)imidazo[1,2-c]pyridin-6-yl]phenyl}methanol;
2-{3-[2-(4-chlorophenyl)-3-fluoroimidazo[1,2-c]pyridin-6-yl]phenyl}propan-2-ol;
2-{3-[3-chloro-2-(4-chlorophenyl)imidazo[1,2-c]pyridin-6-yl]phenyl}propan-2-ol;
[2-fluoro-6-(3-methyl-2-phenylimidazo[1,2-c]pyridin-6-yl)phenyl]methanol;
{2-[2-(4-chlorophenyl)-3-methylimidazo[1,2-c]pyridin-6-yl]-6-fluorophenyl}methanol;
{2-[2-(3-chlorophenyl)-3-methylimidazo[1,2-c]pyridin-6-yl]-6-fluorophenyl}methanol;
{2-[2-(2,4-difluorophenyl)-3-methylimidazo[1,2-c]pyridin-6-yl]-6-fluorophenyl}methanol;
3-chloro-6-(3-methoxymethylphenyl)-2-(4-chlorophenyl)imidazo[1,2-c]pyridine; and
{3-[3-chloro-2-(4-chlorophenyl)imidazo[1,2-c]pyridin-6-yl]-2,6-difluorophenyl}methanol.

11. A pharmaceutical composition comprising a compound of formula (I) according to claim 1 or a pharmaceutically acceptable salt thereof, and one or more pharmaceutically acceptable excipients.

12. A pharmaceutical composition comprising a compound according to claim 10 or a pharmaceutically acceptable salt thereof, and one or more pharmaceutically acceptable excipients.

* * * * *